United States Patent
Nakanishi et al.

(10) Patent No.: US 9,784,694 B2
(45) Date of Patent: Oct. 10, 2017

(54) X-RAY COMPUTED TOMOGRAPHY APPARATUS AND RECONSTRUCTION PROCESSING METHOD

(71) Applicant: Toshiba Medical Systems Corporation, Otawara-shi (JP)

(72) Inventors: Satoru Nakanishi, Utsunomiya (JP); Naruomi Akino, Nasushiobara (JP); Yoshinori Uebayashi, Utsunomiya (JP); Takahiro Goto, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/040,231

(22) Filed: Sep. 27, 2013

(65) Prior Publication Data
US 2014/0029717 A1   Jan. 30, 2014

Related U.S. Application Data

(63) Continuation-in-part of application No. PCT/JP2013/059268, filed on Mar. 28, 2013.

(30) Foreign Application Priority Data

Apr. 11, 2012   (JP) .................................. 2012-090209

(51) Int. Cl.
*G01N 23/04* (2006.01)
*A61B 6/03* (2006.01)
(Continued)

(52) U.S. Cl.
CPC ............. *G01N 23/046* (2013.01); *A61B 6/03* (2013.01); *A61B 6/5205* (2013.01); *G06T 11/003* (2013.01)

(58) Field of Classification Search
CPC ....... A61B 6/032; A61B 6/4233; A61B 6/027; A61B 6/542; A61B 6/5241; A61B 6/4085;
(Continued)

(56) References Cited

U.S. PATENT DOCUMENTS

2002/0141531 A1   10/2002   Taguchi
2007/0201610 A1   8/2007    Adachi et al.
(Continued)

FOREIGN PATENT DOCUMENTS

JP   2002-360562 A   12/2000
JP   2007-252898 A   10/2007
(Continued)

OTHER PUBLICATIONS

International Search Report dated Apr. 23, 2013 in PCT/JP2013/059268 (submitting English translation only).
(Continued)

*Primary Examiner* — Jason McCormack
*Assistant Examiner* — Sean Luck
(74) *Attorney, Agent, or Firm* — Oblon, McClelland, Maier & Neustadt, L.L.P.

(57) ABSTRACT

According to one embodiment, an X-ray computed tomography apparatus includes an X-ray generation unit, an X-ray detection unit, a unit to reconstruct volume data for a reconstruction region having an operator-designated diameter based on projection data, a unit to generate interpolation data based on measurement data to complete projection data for end portions of the reconstruction region wherein the projection data required for reconstructing the volume data of a middle portion of the reconstruction region is acquired as the measurement data, and a unit to decide a width of the end portions based on the set radiation range along the top's
(Continued)

longitudinal direction, reconstruction region's diameter, and object's imaging target portion.

7 Claims, 13 Drawing Sheets

(51) Int. Cl.
*A61B 6/00* (2006.01)
*G06T 11/00* (2006.01)

(58) Field of Classification Search
CPC ............ G01N 23/046; G01N 2223/419; G06T 11/005; G06T 11/003
See application file for complete search history.

(56) References Cited

U.S. PATENT DOCUMENTS

| | | |
|---|---|---|
| 2008/0205587 A1 | 8/2008 | Nakanishi |
| 2009/0175562 A1* | 7/2009 | Pan et al. .................. 382/312 |
| 2011/0286574 A1* | 11/2011 | Suzuki .................. 378/8 |
| 2012/0093281 A1* | 4/2012 | Zamyatin et al. .............. 378/15 |
| 2012/0257709 A1* | 10/2012 | Oota et al. .................. 378/4 |

FOREIGN PATENT DOCUMENTS

| | | |
|---|---|---|
| JP | 2008-237886 A | 10/2008 |
| JP | 2009-279301 A | 12/2009 |
| WO | WO 2010/100996 A1 | 9/2010 |

OTHER PUBLICATIONS

Japanese Office Action issued in Japanese Patent Application No. 2012-090209 dated Mar. 8, 2016.
International Search Report dated Apr. 23, 2013 for PCT/JP2013/059268 filed Mar. 28, 2013 with English translation of categories.
International Written Opinion dated Apr. 23, 2013 for PCT/JP2013/059268 filed Mar. 28, 2013.

* cited by examiner

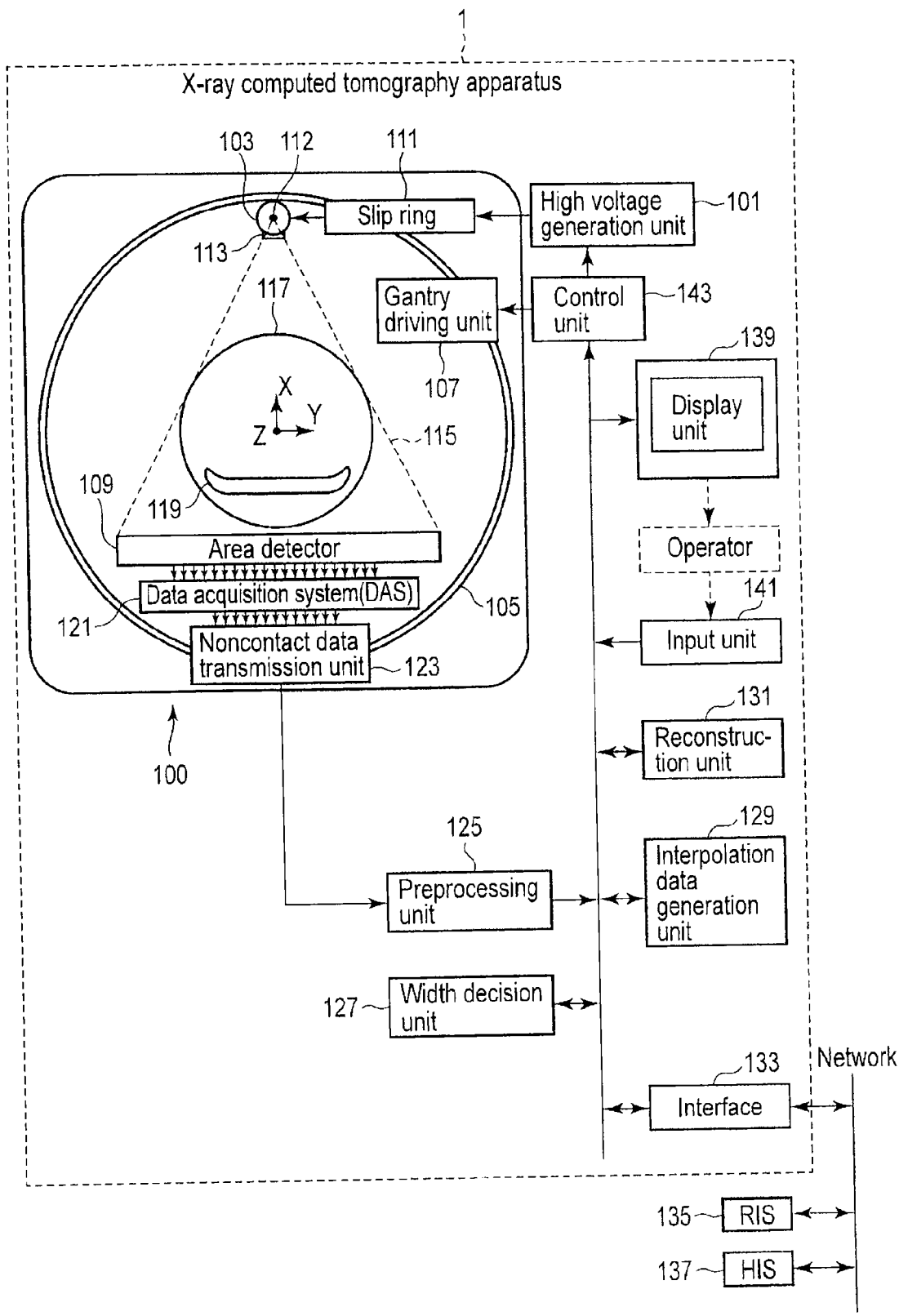
F I G. 1

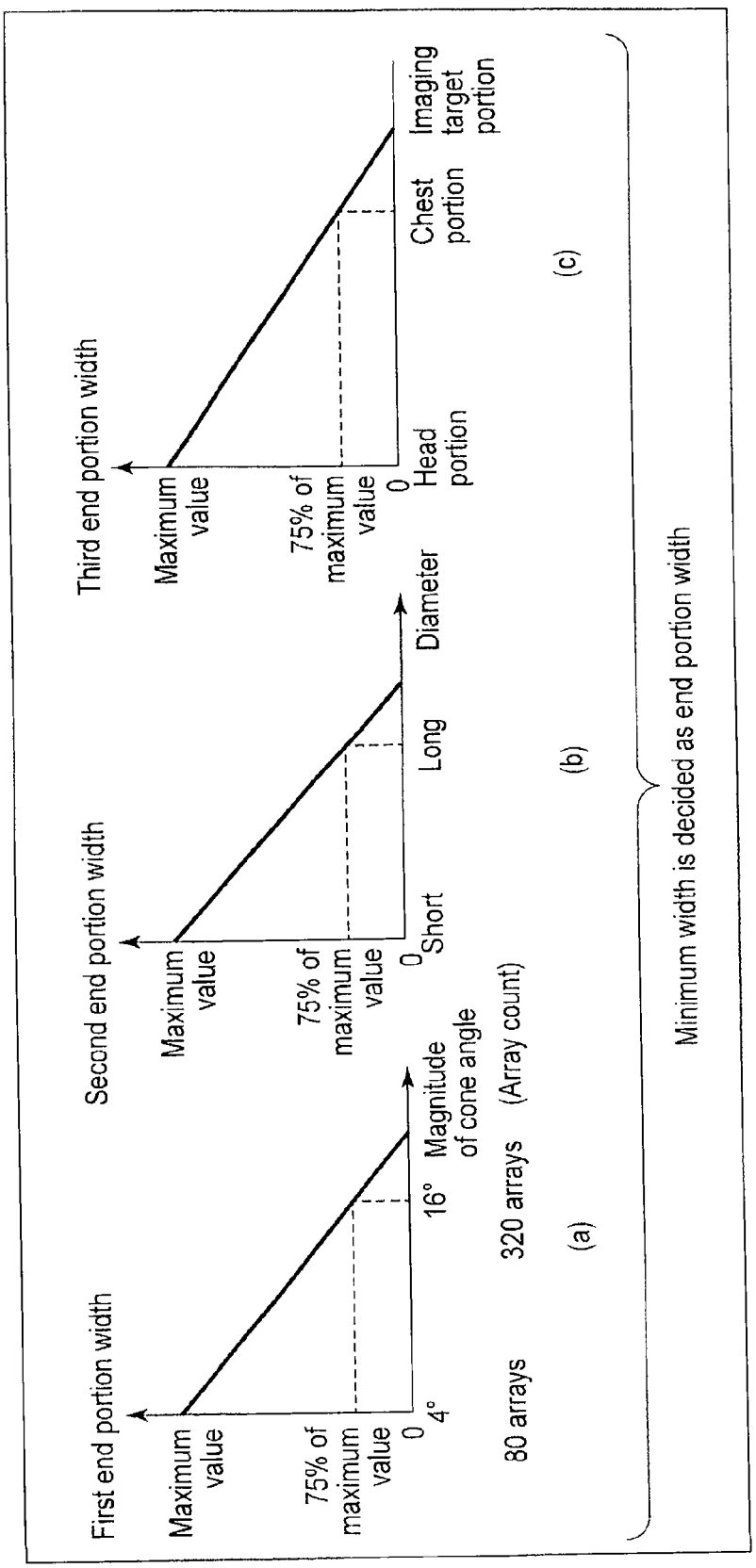
F I G. 2

|  |  | End portion width |
|---|---|---|
| Cone angle (array count) | 16° (320 arrays) | 75% of maximum value |
|  | 4° (80 arrays) | Maximum value |
| Diameter | Long | 75% of maximum value |
|  | Short | Maximum value |
| Imaging target portion | Chest portion, abdominal portion | 75% of maximum value |
|  | Head portion | Maximum value |
Minimum end portion width is decided as width of end portion used for reconstruction
F I G. 3
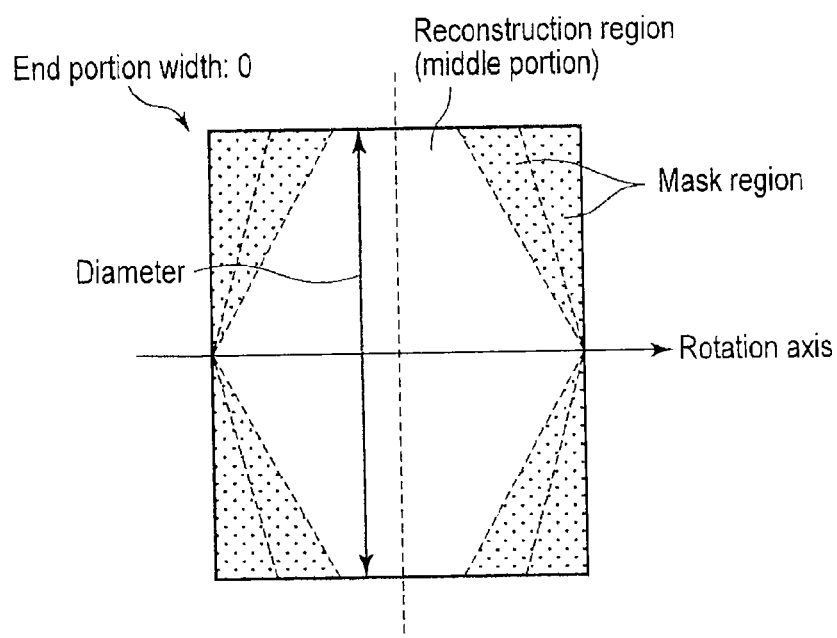
F I G. 4

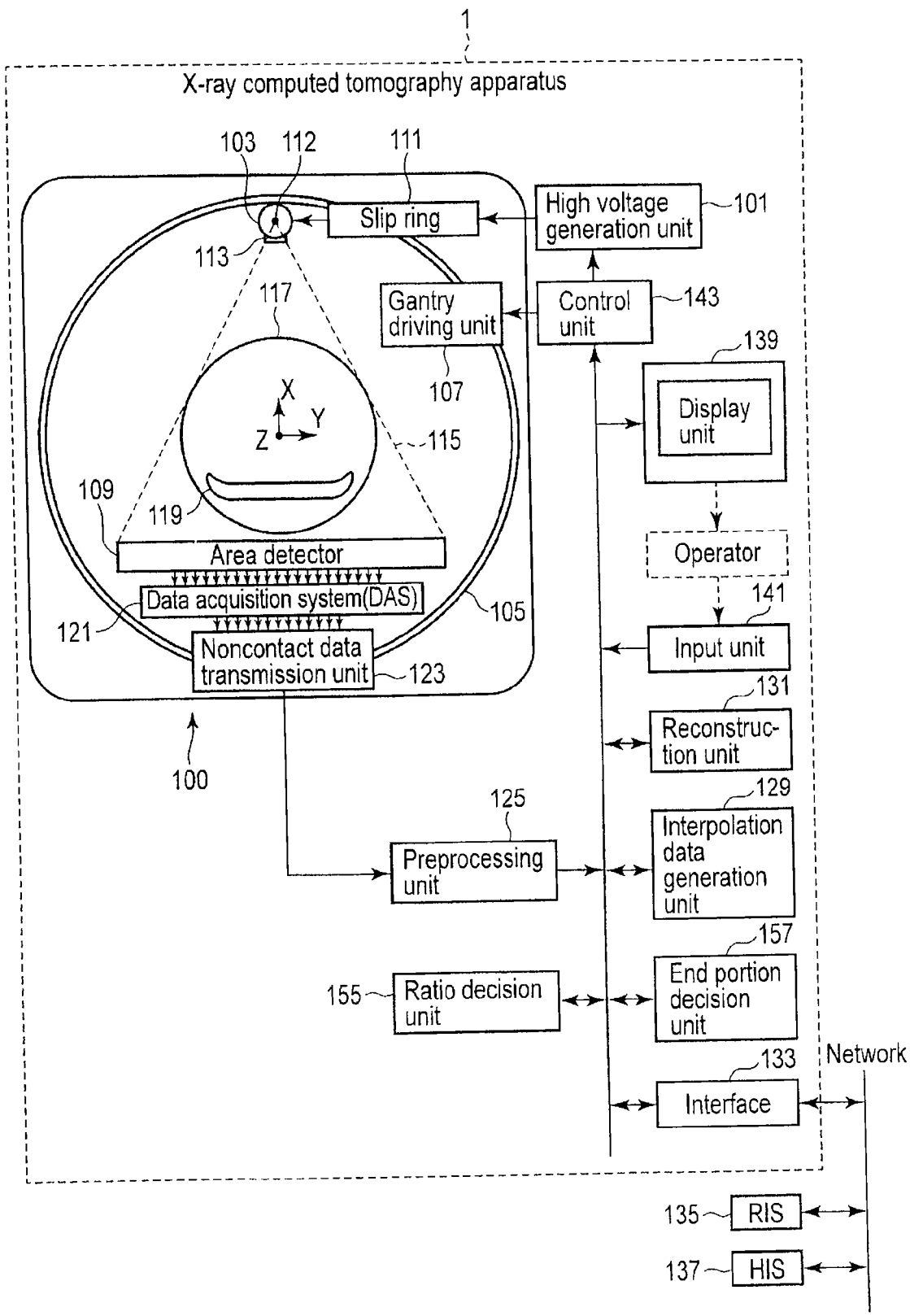
F I G. 11

| | | End portion expansion ratio (%) |
|---|---|---|
| Cone angle (array count) | 16° (320 arrays) | 75 |
| | 4° (80 arrays) | 100 |
| Diameter | Long | 75 |
| | Short | 100 |
| Imaging target portion | Chest portion, abdominal portion | 75 |
| | Head portion | 100 |
Minimum end portion expansion ratio is decided as expansion ratio of end portion used for reconstruction
F I G. 13
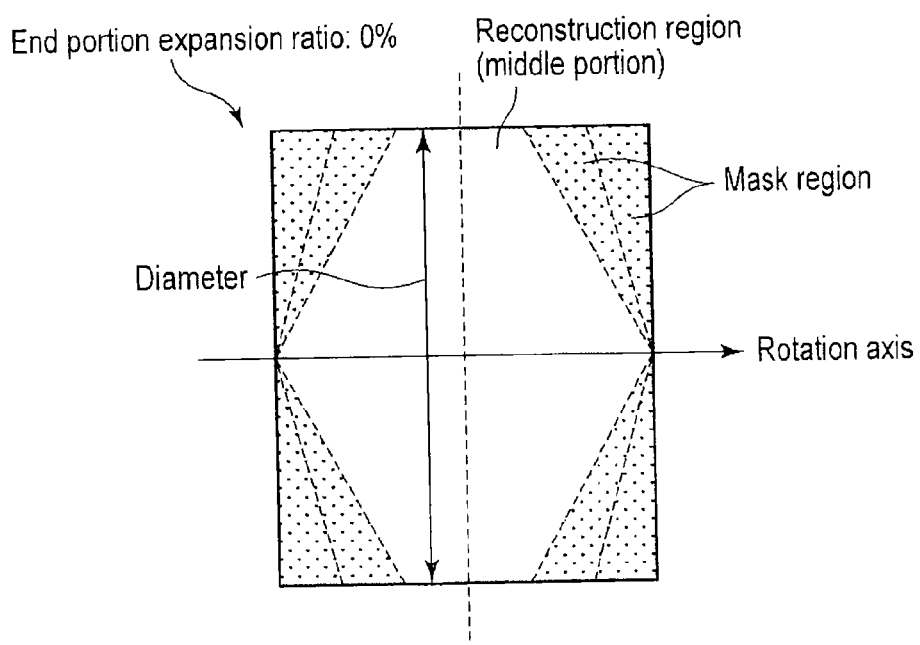
F I G. 14

X-RAY COMPUTED TOMOGRAPHY APPARATUS AND RECONSTRUCTION PROCESSING METHOD

CROSS REFERENCE TO RELATED APPLICATIONS

This application is a Continuation in Part Application of PCT Application No. PCT/JP2013/059268, filed Mar. 28, 2013 and based upon and claiming the benefit of priority from Japanese Patent Application No. 2012-090209, filed Apr. 11, 2012, the entire contents of all of which are incorporated herein by reference.

FIELD

Embodiments described herein relate generally to an X-ray computed tomography apparatus and a reconstruction processing method.

BACKGROUND

An X-ray CT (Computed Tomography) apparatus including an area detector reconstructs volume data based on the projection data obtained by scanning an object along a circular orbit. Projection data corresponds to the data obtained by performing line integration of X-ray attenuation coefficients along X-rays. In this case, a region (to be referred to as a measurement data complete region hereinafter) where projection data in an angular range (e.g., 360°) necessary for reconstruction processing is completely prepared in the form of measurement data is a region (a region inside the shape of a truncated bicone) inside the rotating body obtained by, for example, rotating the lower base of an isosceles trapezoid about a rotation axis. A mask which is covered to inhibit the execution of reproduction processing is provided for a region (to be referred to as a mask region hereinafter), of a region where projection data has been acquired, where projection data in an angular range (e.g., 360°) necessary for reconstruction processing is not completely prepared in the form of measurement data. FIG. 18 is a view showing a measurement data complete region and mask regions together with an X-ray tube and an X-ray radiation range. In order to reconstruct the volume data obtained by approximating the rotating body to an almost cylindrical shape by reducing mask regions (this processing is called mask region reconstruction or body axis direction region expansion reconstruction and will be called mask region reconstruction hereinafter), it is necessary to perform dedicated reconstruction using measurement data and interpolation data generated by interpolating the measurement data.

Step and shoot scanning uses a plurality of volume data generated by using mask region reconstruction when coupling the data along the body axis direction of the object. The volume data coupled along the body axis direction of an object will be referred to as a wide-volume. The use of mask region reconstruction can reduce a region (to be referred to as an overlap region hereinafter) where overlapping occurs between a plurality of volume data to be coupled. A reduction in overlap region will contribute to a reduction in exposure to radiation of an object in step and shoot scanning and generation of wide-volume.

It is not, however, that it is possible to execute mask region reconstruction under any conditions. For example, a portion exhibiting a large change in CT value in the body axis direction is located at a cone angle end, the quality of an image at the portion deteriorates. For this reason, in mask region reconstruction, image quality deteriorates depending on the portion.

BRIEF DESCRIPTION OF THE DRAWING

FIG. 1 is a view showing the arrangement of an X-ray computed tomography apparatus according to the first embodiment.

FIG. 2 is a view showing an example of the first to third width correspondence tables according to the first embodiment.

FIG. 3 is a view showing an example of a correspondence table between end portion widths and a plurality of types of conditions (a cone angle, the FOV of the first region, and an imaging target portion) according to the first embodiment.

FIG. 4 is a view showing an example of a middle portion, mask regions, and rotation axis when the end portion width is 0 or before an end portion width is decided according to the first embodiment.

FIG. 11 is a view showing the arrangement of an X-ray computed tomography apparatus according to the second embodiment.

FIG. 13 is a view showing an example of a correspondence table between expansion ratios and a plurality of types of conditions (a cone angle, the FOV of the first region, and an imaging target portion) according to the second embodiment.

FIG. 14 is a view showing an example of a middle portion, mask regions, and a rotation axis when the expansion ratio is 0 or before an end portion expansion ratio is decided according to the second embodiment.

DETAILED DESCRIPTION

Figure 5:
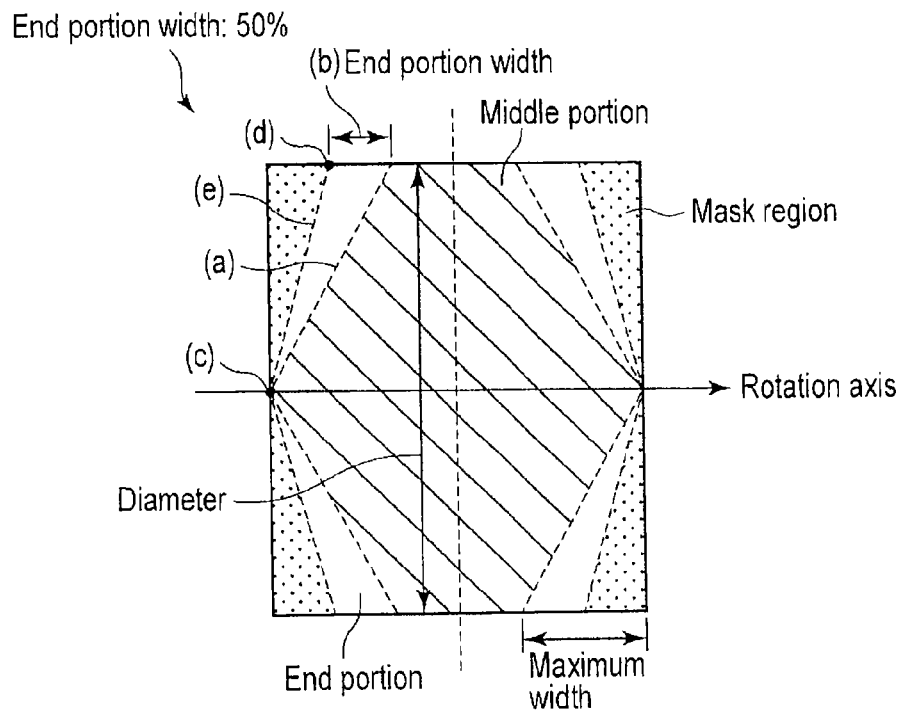
FIG. 5 is a view showing an example of a middle portion, end portions, mask regions, and rotation axis when the end portion width is 50% of the maximum width according to the first embodiment.

In general, according to one embodiment, an X-ray computed tomography apparatus includes an X-ray generation unit, a two-dimensional array type or multislice type X-ray detection unit, a reconstruction unit, an interpolation data generation unit, and a width decision unit.

The X-ray generation unit generates a cone-beam X-ray. The two-dimensional array type or multislice type X-ray detection unit detects the X-ray from the X-ray generation unit through an object on a top. The reconstruction unit reconstructs volume data for a reconstruction region based on projection data corresponding to an output from the X-ray detection unit, the reconstruction region having a diameter designated by an operator. The interpolation data generation unit generates interpolation data based on measurement data in order to complete the projection data for end portions of the reconstruction region, wherein the projection data required for reconstructing the volume data of a middle portion between the both end portions of the reconstruction region is acquired as the measurement data. The width decision unit decides a width of the end portions based on a set radiation range for radiation of the X-ray along a longitudinal direction of the top, the diameter of the reconstruction region, and an imaging target portion of the object.

An embodiment of an X-ray computed tomography apparatus 1 according to an embodiment will be described below with reference to the accompanying drawings. Note that the X-ray computed tomography apparatus 1 includes various types such as a rotate/rotate-type apparatus in which an X-ray tube 103 and an area detector 109 rotate together around an object and a stationary/rotate-type apparatus in which many detectors arranged in the form of a ring are fixed and only the X-ray tube 103 rotates around an object. Either type can be applied to this embodiment. In addition, in order to reconstruct an image, projection data corresponding to one rotation (360°) around an object. The half scan method requires projection data corresponding to 180°+ fan angle. Either reconstruction scheme can be applied to the embodiment. For ease of explanation, reconstruction using projection data corresponding to one rotation (360°) around an object will be referred to as FS (Full Scan) hereinafter.

As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor such as selenium by X-rays and migration of the electron-hole pairs to an electrode, i.e., a photoconductive phenomenon. As an X-ray detection element, either of these schemes can be used. Recently, with advances toward the commercialization of a so-called multi-tube type X-ray computed tomography apparatus having a plurality of pairs of X-ray tubes 103 and X-ray detectors 109 mounted on a rotating ring 105, related techniques have been developed. This embodiment can be applied to both a conventional single-tube type X-ray computed tomography apparatus and a multi-tube type X-ray computed tomography apparatus. The single-tube type X-ray computed tomography apparatus will be exemplified here.

Note that the same reference numerals denote constituent elements having almost the same functions and arrangements in the following description, and a repetitive description will be made only when required.

First Embodiment

FIG. 1 is a view showing the arrangement of the X-ray computed tomography apparatus 1 according to the first embodiment. The X-ray computed tomography apparatus 1 according to the first embodiment includes a gantry 100, a high voltage generation unit 101, a preprocessing unit 125, a width decision unit 127, an interpolation data generation unit 129, a reconstruction unit 131, an interface 133, a display unit 139, an input unit 141, and a control unit 143.

The high voltage generation unit 101 generates a high voltage to be applied to the X-ray tube 103. The high voltage generation unit 101 generates a plurality of high voltages under the control of the control unit 143 (to be described later).

A rotation support mechanism is housed in the gantry 100. The rotation support mechanism is constituted by the rotating ring 105, a ring support mechanism which supports the rotating ring 105 so as to make it rotatable about a rotation axis Z, and a gantry driving unit 107 (electric motor) which rotates the ring. The rotating ring 105 is equipped with the X-ray tube 103 and the area detector (X-ray detection unit) 109 which is called a two-dimensional array type or multi-array type detector.

The X-ray tube 103 receives a voltage and a current from the high voltage generation unit 101 via a slip ring 111 and emits X-rays from an X-ray focal point 112. Note that a combination of the X-ray tube 103 and the high voltage generation unit 101 will be referred to as an X-ray generation unit 102.

A collimator 113 is attached to the X-ray irradiation window on the front surface of the X-ray tube 103. The collimator 113 includes a plurality of collimator plates. The plurality of collimator plates shape X-rays emerging from the X-ray focal point 112 into, for example, a cone beam shape (pyramidal shape). More specifically, the control unit 143 (to be described later) drives the plurality of collimator plates to obtain a cone angle for obtaining measured projection data with a preset slice thickness. At least two collimator plates (to be referred to as cone angle collimators hereinafter) of the plurality of collimator plates are independently driven in the opening width corresponding to a cone angle under the control of the control unit 143.

Dotted lines 115 in FIG. 1 indicate an X-ray radiation range. The X-axis is a straight line which is perpendicular to the rotation axis Z and extends upward in the vertical direction. The Y-axis is a straight line perpendicular to the X- and Z-axes and the rotation axis Z.

Note that the collimator 113 drives the cone angle collimator based on the set radiation range associated with an X-ray radiation range setting along the long-axis direction of a top 119 (to be described later). A set radiation range (parameter) includes, for example, a cone angle, the number of arrays of the X-ray detector (to be described later), and a detector width.

The area detector 109 is mounted at a position and angle at which it faces the X-ray tube 103 through the rotation axis Z. The area detector 109 includes a plurality of X-ray detection elements. Assume that a single X-ray detection element forms a single channel. A plurality of channels are two-dimensionally arranged in two directions, i.e., the slice direction and the arc direction (channel direction) which is perpendicular to the rotation axis Z and whose radius corresponds to the distance from the focal point of X-rays, as a center, from which X-rays emerge, to the center of the light-receiving portion of an X-ray detection element corresponding to one channel. In a two-dimensional arrangement, a plurality of arrays each having a plurality of channels one-dimensionally arranged along the channel direction are arranged in the slice direction.

The area detector 109 having such two-dimensional X-ray detection element arrays may be formed by arranging, in the slice direction, a plurality of arrays each including the plurality of modules one-dimensionally arranged in the nearly arc direction. The area detector 109 may be constituted by a plurality of modules each having a plurality of X-ray detection elements arranged in an array. The respective modules are one-dimensionally arranged in nearly the arc direction along the channel direction. The number of X-ray detection elements arranged in the slice direction will be referred to as an array count hereinafter. The length of the area detector 109 in the slice direction will be referred to as a detector width.

When performing imaging or scanning, the operator inserts an object P placed on the top 119 into a cylindrical imaging region 117 between the X-ray tube 103 and the area detector 109. A data acquisition system (to be referred to as a DAS hereinafter) 121 is connected to the output of the area detector 109.

The DAS 121 is provided with, for each channel, an I-V converter which converts the current signal obtained via each channel of the area detector 109 into a voltage, an integrator which periodically integrates these voltage signals in synchronism with an X-ray irradiation period, an amplifier which amplifies an output signal from the integrator, and an analog/digital converter which converts an output signal from the amplifier into a digital signal. The data (pure raw data) output from the DAS 121 is transmitted to the preprocessing unit 125 via a noncontact data transmission unit 123 using magnetic transmission/reception or optical transmission/reception. The DAS 121 changes the integration interval of the integrator in accordance with a scan under the control of the control unit 143 (to be described later).

The preprocessing unit 125 preprocesses the pure raw data output from the DAS 121. The preprocessing includes, for example, sensitivity nonuniformity correction processing between channels and the processing of correcting an extreme decrease in signal intensity or signal omission due to an X-ray absorber, mainly a metal portion. The data (called raw data or projection data; projection data in this case) output from the preprocessing unit 125 and the interpolation data generation unit 129 immediately before reconstruction processing is stored in a storage unit (not shown) including a magnetic disk, magneto-optical disk, or semiconductor memory in association with data representing view angles at the time of data acquisition. Data of projection data which is output from the preprocessing unit 125 is called measurement data. In addition, data of projection data, which is generated by the interpolation data generation unit 129 (to be described later) by interpolation processing based on measurement data will be referred to as interpolation data.

For the sake of descriptive convenience, assume that a set of projection data acquired nearly at the same time with one shot at the same view angle throughout the channels defined by a cone angle will be referred to as a projection data set. The respective view angles are represented by angles in the range of 0° to 360° which represent the respective positions on a circular orbit centered on the rotation axis Z, along which the X-ray tube 103 revolves, with the angle of the uppermost portion on the circular orbit in an upward vertical direction from the rotation axis Z being 0°. Note that projection data of a projection data set which corresponds to each channel is identified by a view angle, cone angle, and channel number.

The reconstruction region for which reconstruction processing is performed by the reconstruction unit 131 (to be described later) is constituted by a middle portion and end portions. The middle portion is a region where all the projection data necessary for the reconstruction of volume data (to be described later) is completely prepared. The middle portion has the diameter input by the input unit 141 (to be described later). The diameter does not correspond to a region to be imaged but corresponds to the maximum length of the FOV (Field Of View) of a reconstruction region (to be referred to as a reconstruction FOV hereinafter) which is perpendicular to the rotation axis. A middle portion has the shape of a rotating body obtained by, for example, rotating the lower base of an isosceles trapezoid having half of the diameter (to be referred to as the radius hereinafter) about a rotation axis. This rotating body corresponds to the maximum volume of the middle portion. The diameter corresponds to twice the height of the isosceles trapezoid, i.e., the diameter of the rotating body. The rotating body (middle portion) has a hexagonal sectional shape obtained by coupling the two lower bases of two congruent isosceles trapezoids. Note that the middle portion may be a columnar shape having a length along the rotation axis as a height and the diameter as a diameter. At this time, a columnar shape on a slice including a rotating axis is a rectangle.

An one or end portions are a region where the projection data necessary for the reconstruction of volume data (to be described later) is completely prepared by measurement data and the interpolation data generated from the measurement data by interpolation. The width of the end portion in the rotation axis direction (to be referred to as an end portion width hereinafter) is defined by a length along a straight line which passes through a point spaced apart from the rotation axis by the radius and is parallel to the rotation axis. The maximum width, of the end portion widths, which allows expansion is a value half of the difference value obtained by subtracting the upper base of a sectional shape of the middle portion from the lower base when the sectional shape is an isosceles trapezoid. If the middle portion of the middle portion is defined by a columnar shape, the maximum width corresponds to half of the difference value obtained by subtracting the height of the column from the length of the lower base of an isosceles trapezoid. When the width decision unit 127 (to be described later) decides a maximum width as an end portion width, a reconstruction region has a columnar shape. A sectional shape of a reconstruction region on a slice including a rotation axis can be expanded from a hexagonal shape to a rectangular shape while the diameter is maintained in accordance with the end portion width.

The width decision unit 127 decides an end portion width based on the scan conditions and reconstruction conditions used for reconstruction processing which are input via the input unit 141 (to be described later). Scan conditions (scan protocol) include, for example, the magnitude of a cone angle, a set radiation range such as an array count corresponding to the magnitude of a cone angle or a detector width, and an imaging target portion of an object which is set by a scanogram. Reconstruction conditions include a reconstruction function used for reconstruction processing and a diameter.

Note that the width decision unit 127 may decide an imaging target portion in accordance with a synchronization target of a synchronous scan in a scan protocol and decide an end portion width based on the decided imaging target portion. If, for example, a synchronous scan is an ECG scan, the width decision unit 127 decides a chest portion as an imaging target portion. If a synchronous scan is a respiratory gated scan, the width decision unit 127 decides an abdominal portion as an imaging target portion. The width decision unit 127 may decide an imaging target portion in accordance with a reconstruction function setting.

More specifically, the width decision unit 127 includes a memory (not shown). The memory stores at least one of the first width correspondence table between cone angles and first end portion widths, the second width correspondence table between diameters and second end portion widths, and the third width correspondence table between imaging target portions of an object and third end portion widths. The width decision unit 127 receives scan conditions or reconstruction conditions associated with the stored correspondence table and decides an end portion width. If, for example, the memory stores the first width correspondence table, the width decision unit 127 decides an end portion width based on the cone angle or array count (or detector width) input via the input unit 141 and the first width correspondence table. When the width decision unit 127 receives, for example, an array count of 80 or detector width corresponding to a cone angle of 4° via the input unit 141, the width decision unit 127 decides an end portion width as a maximum width. At this time, a reconstruction region has a cylindrical shape.

If the memory of the width decision unit 127 stores the first to third width correspondence tables, the width decision unit 127 decides the first to third end portion widths respectively corresponding to the first to third width correspondence tables based on the scan conditions or reconstruction conditions input via the input unit 141. The width decision unit 127 decides the minimum one of the first to third end portion widths as an end portion width of a reconstruction region.

FIG. 2 shows an example of the first width correspondence table (a), second width correspondence table (b), and third width correspondence table (c). Note that the memory may store a correspondence table (multivariable width correspondence table) of end portion widths corresponding to a plurality of types of conditions (cone angles, array counts, detector widths, diameters, and imaging target portions) like those described in FIG. 3 in place of the first to third width correspondence tables. Note that the memory may store the fourth width correspondence table between reconstruction functions and fourth end portion widths. The width decision unit 127 reads out the first to fourth end portion widths respectively corresponding to the first to fourth width correspondence tables based on the cone angle (or the array count or detector width), diameter, imaging target portion, and reconstruction function input from an RIS (Radiology Information System) 135 or an HIS (Hospital Information System) 137 via the input unit 141 (to be described later) and the interface 133. The width decision unit 127 decides the minimum one of the read first to fourth end portion widths as the end portion width of an end portion of the reconstruction region. The width decision unit 127 outputs the decided end portion width to the interpolation data generation unit 129. The width decision unit 127 decides an end portion of the reconstruction region based on the decided end portion width.

The region of an end portion will be described with reference to FIGS. 4, 5, and 6 by exemplifying a case in which a middle portion on a slice including a rotation axis has a hexagonal sectional shape. FIG. 4 is a view showing an example of a reconstruction region, mask regions, and a rotation axis when the end portion width is 0 or before an end portion width is decided. In this case, the reconstruction region is identical to the middle region.

FIG. 5 is a view showing an example of end portions, a middle portion, mask regions, and a rotation axis when the end portion width is 50% of the maximum width. The region of the end portion on a slice including a rotation axis is defined by sides (a), of the sides of a hexagon, which are not parallel to the rotation axis, end portion widths (b) parallel to the rotation axis, and sides (e) connecting vertices (c), of the vertices of the hexagon, which are located on the rotation axis to points (d) obtained by extending sides, of the six sides of the hexagon, which are parallel to the rotation axis throughout the end portion widths.

Figure 6:
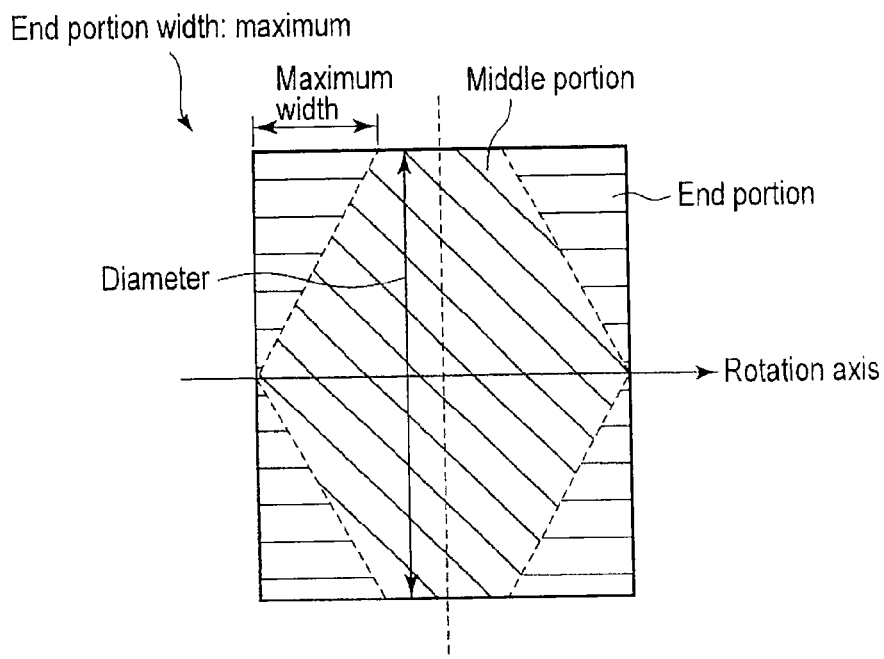
FIG. 6 is a view showing an example of a middle portion, end portions, and rotation axis when the end portion width is the maximum width according to the first embodiment.

FIG. 6 is a view showing an example of end portions, a middle portion, and a rotation axis when the end portion width is the maximum width. In this case, a reconstruction region on a slice including the rotation axis has a rectangular shape. The reconstruction region has a cylindrical shape in terms of three dimensions.

The interpolation data generation unit 129 interpolates projection data associated with a region (to be referred to as a measurement data unacquired region hereinafter) of each end portion where measurement data corresponding to 360° around an object has not been acquired, by using measurement data, based on the end portion width output from the width decision unit 127. The interpolation data generation unit 129 outputs the generated interpolation data in the measurement data unacquired region to the reconstruction unit 131 (to be described later). More specifically, the interpolation data generation unit 129 generates interpolation data by performing interpolation processing (e.g., extrapolation processing) based on measurement data in a region (to be referred to an FSPBS region hereinafter), of the measurement data unacquired region, where both FS (Full Scan) reconstruction and PBS (Pixel-Based Sector) reconstruction are executed. PBS reconstruction will be described in detail with reference to the reconstruction unit 131.

The reconstruction unit 131 has a function of reconstructing a three-dimensional image in a nearly cylindrical shape (to be referred to as volume data) associated with a reconstruction region (a middle portion and FSPBS regions) by the Feldkamp method or the cone beam reconstruction method based on a projection data set acquired at view angles in the range of 360°. The reconstruction processing unit 131 also has a function of reconstructing a two-dimensional image (tomographic image) by, for example, the fan beam reconstruction method (also called the fan beam convolution back projection method) or the filtered back projection method. The Feldkamp method is a reconstruction method to be used when projection rays intersect a reconstruction plane like a cone beam. The Feldkamp method is an approximate image reconstruction method of performing processing by regarding a projection beam as a fan projection beam on the premise that the cone angle is small, whereas back projection processing is performed along a ray in scanning operation. The cone beam reconstruction method is a reconstruction method which corrects projection data in accordance with the angle of a ray relative to a reconstruction plane as a method which suppresses cone angle errors more than the Feldkamp method.

The reconstruction unit 131 reconstructs volume data (to be referred to as end portion FS volume data hereinafter) associated with the FSPBS region of each end portion by the Feldkamp method or the like based on a projection data set constituted by interpolation data and measurement data. The reconstruction unit 131 then reconstructs volume data (to be referred to as end portion PBS volume data hereinafter) associated with each FSPBS region by the PBS reconstruction method based on measured projection data associated with the FSPBS region. The PBS reconstruction method is a method of deciding a plurality of rays passing through reconstruction pixels and calculating the CT values of the reconstruction pixels by using projection data corresponding to the rays. The reconstruction unit 131 generates volume data (to be referred to as feathering volume data hereinafter) in the FSPBS region by performing weighed addition (to be referred to as feathering hereinafter) of end portion FS volume data and end portion PBS volume data.

The reconstruction unit 131 generates volume data associated with a region (to be referred to as PBS volume data hereinafter) obtained by removing an FSPBS region from each end portion by the PBS reconstruction method based on measurement data. The reconstruction unit 131 generates volume data associated with a reconstruction region based on volume data associated with a middle portion, feathering volume data, and PBS volume data.

The interface 133 connects the X-ray computed tomography apparatus 1 to an electronic communication line (to be referred to as a network hereinafter). The RIS 135 and the HIS 137 are connected to the network.

The display unit 139 displays the medical image reconstructed by the reconstruction unit 131, a scanogram, and an input window for inputting scan conditions to be set for X-ray computed tomography, reconstruction conditions associated with reconstruction processing, and the like.

The input unit 141 inputs various types of instructions, commands, information, selections, and settings from the operator to the X-ray computed tomography apparatus 1. The input instructions, commands, information, selections, and settings are output to the control unit 143 (to be described later). Although not shown, the input unit 141 includes a trackball, switch buttons, a mouse, and a keyboard for, for example, setting an ROI (Region Of Interest). The input unit 141 inputs a scan range for the scanogram generated and displayed by imaging (to be referred to as scanography hereinafter) for deciding a scan start position, imaging conditions, and the like for an object.

The input unit 141 detects the coordinates of the cursor displayed on a display screen, and outputs the detected coordinates to the control unit 143. Note that the input unit 141 may be a touch panel provided to cover the display screen. In this case, the input unit 141 detects touched and designated coordinates by a coordinate reading principle such as an electromagnetic induction scheme, magnetostriction scheme, or a pressure-sensitive scheme, and outputs the detected coordinates to the control unit 143.

The control unit 143 functions as the main unit of the X-ray computed tomography apparatus 1. The control unit 143 includes a CPU and a memory (which are not shown). The control unit 143 controls the high voltage generation unit 101, the gantry 100, and the like to perform X-ray computed tomography based on the examination schedule data and control programs stored in a memory (not shown). More specifically, the control unit 143 temporarily stores instructions from the operator, which are sent from the input unit 141, the RIS 135, and the HIS 137, and the like in a memory (not shown). The control unit 143 controls the high voltage generation unit 101, the gantry 100, and the like based on these pieces of information temporarily stored in the memory. The control unit 143 reads out control programs for executing predetermined image generation and display and the like from a storage unit (not shown), expands the program in a memory of the control unit 143, and executes computation, processing, and the like associated with various types of processing.

The control unit 143 controls the high voltage generation unit 101, the collimator 113, and the like to execute imaging (to be referred to as scanography hereinafter) for an object to decide a scan start position, imaging conditions, and the like for the object. The control unit 143 controls the display unit 139 to display a scanogram of the object which is generated by scanography.

(End Portion Width Decision Reconstruction Function)

The end portion width decision reconstruction function is a function of deciding an end portion width based on at least either scan conditions or reconstruction conditions and reconstructing volume data associated with a reconstruction region. Processing (to be referred to as width decision reconstruction processing hereinafter) based on the end portion width decision reconstruction function will be described below.

Figure 7:
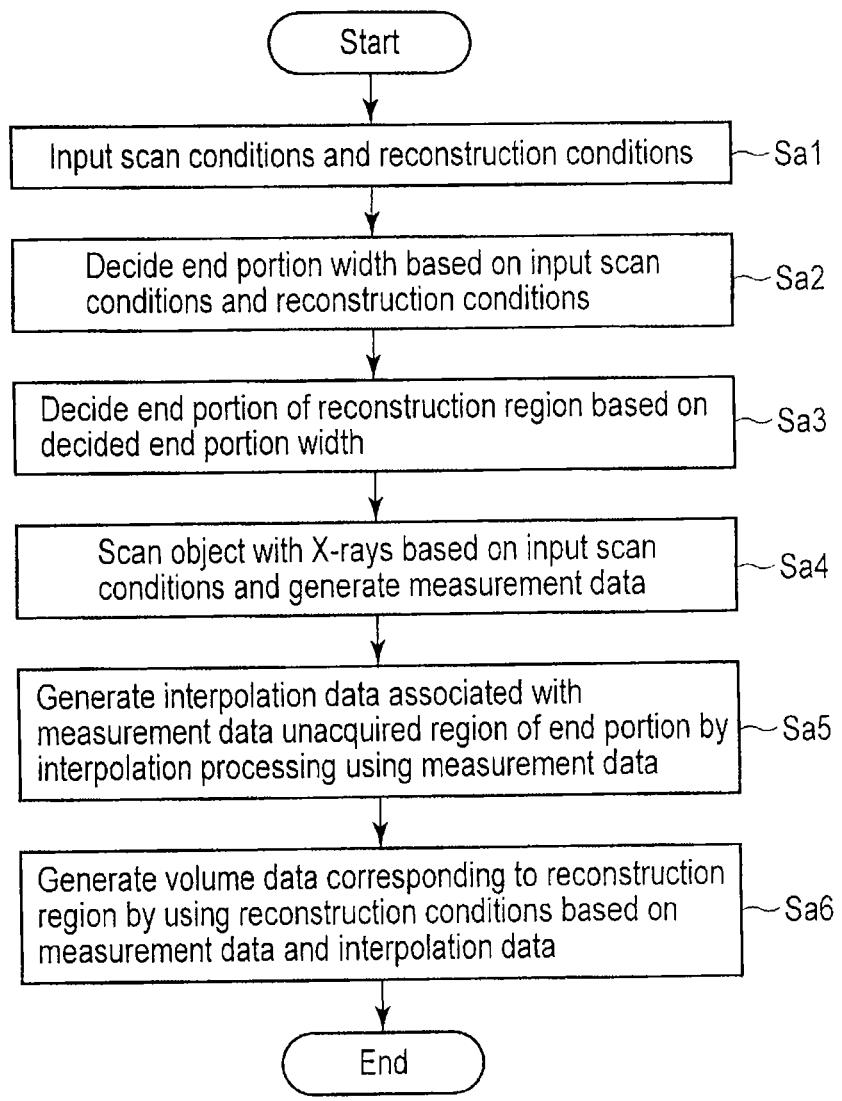
FIG. 7 is a flowchart showing an example of a procedure for width portion width decision reconstruction processing according to the first embodiment.

FIG. 7 is a flowchart showing an example of a procedure for width decision reconstruction processing.

The apparatus executes scanography for an object. The operator inputs scan conditions, reconstruction conditions, and the like via the input unit 141 based on the image generated by scanography (step Sa1). The apparatus decides an end portion width based on the input scan conditions and reconstruction conditions (step Sa2). The apparatus decides each end portion of the reconstruction region based on the decided end portion width (step Sa3). The apparatus scans the object with cone-beam X-rays in accordance with the input scan conditions and generates measurement data (step Sa4). Interpolation processing using the measurement data generates interpolation data associated with the measurement data unacquired region of the end portion (step Sa5). The apparatus generates the volume data associated with the reconstruction region by using the reconstruction conditions based on the measurement data and the interpolation data (step Sa6).

(Modification)

This modification differs from the first embodiment in that the apparatus decides the movement amount (to be referred to as the top movement amount hereinafter) of the top 119 along the long axis direction (to be referred to as the top long axis direction hereinafter) of the top 119 based on the length of a reconstruction region (to be referred to as the reconstruction axis length hereinafter) in the rotation axis direction and moves the top 119 in accordance with the decided top movement amount in step and shoot scanning.

Figure 8:
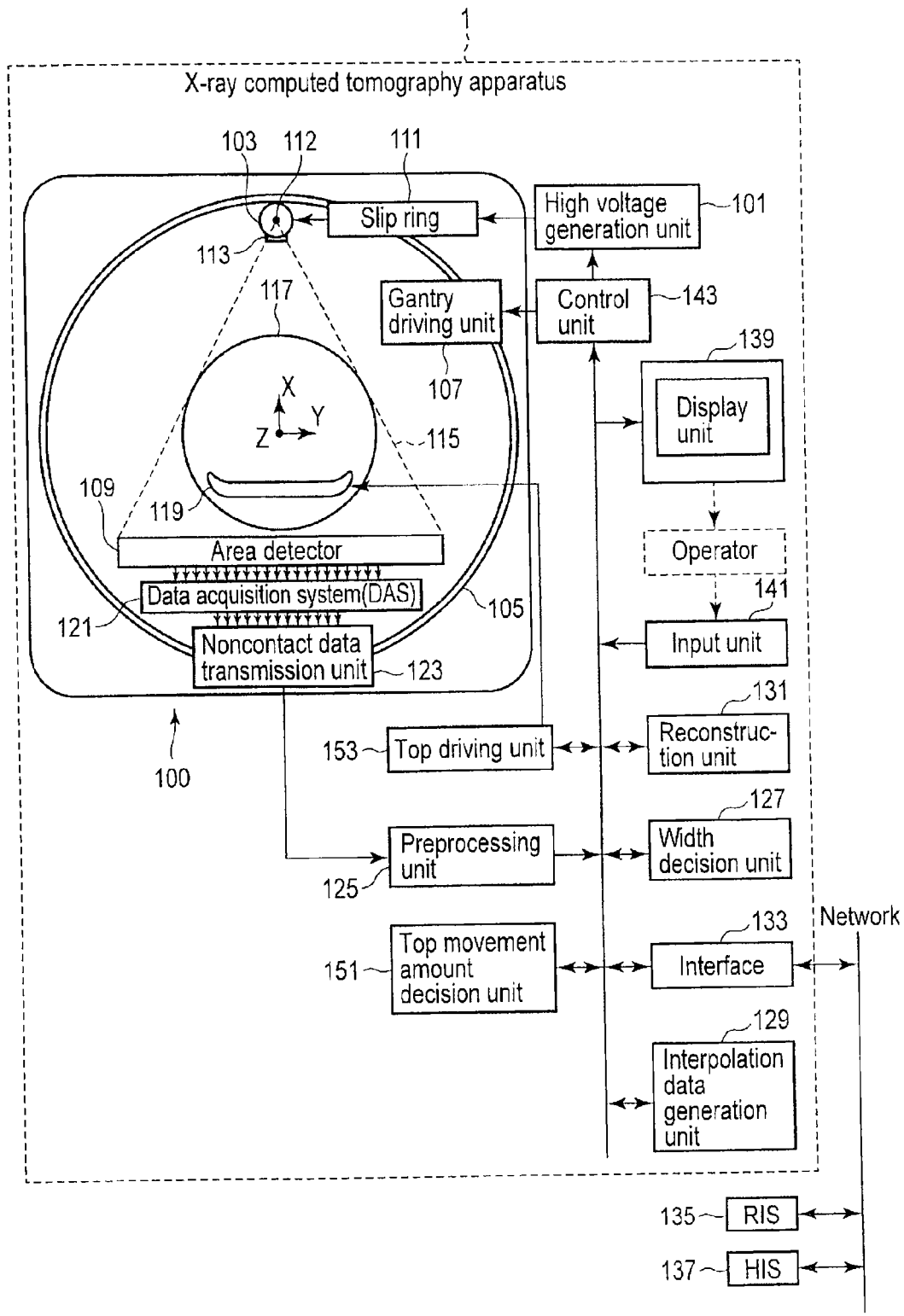
FIG. 8 is a view showing the arrangement of an X-ray computed tomography apparatus according to a modification of the first embodiment.

FIG. 8 is a view showing an example of the arrangement of an X-ray computed tomography apparatus according to a modification of the first embodiment.

Figure 9:
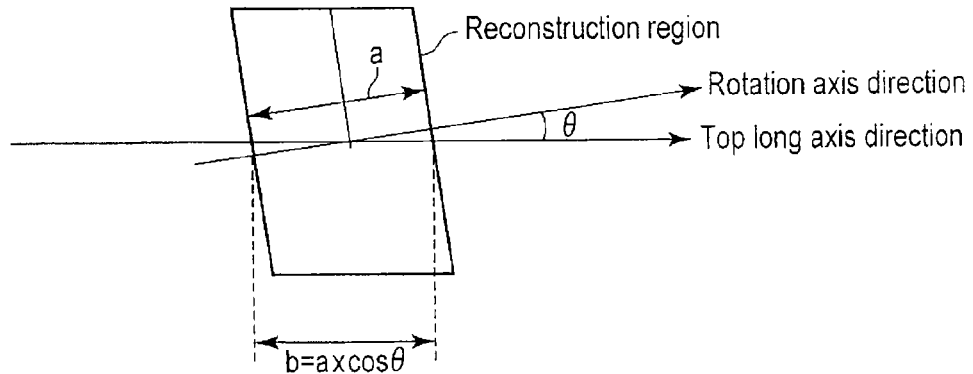
FIG. 9 is a view showing an example of expressing a top movement amount b by using a length a of a reconstruction region in the rotation axis direction and a tilt angle θ when executing step and shoot scanning upon tilting the gantry through the tilt angle θ according to a modification of the first embodiment.

A top movement amount decision unit 151 decides a top movement amount along the top long axis direction based on the reconstruction axis length. More specifically, the top movement amount decision unit 151 decides the reconstruction axis length as a top movement amount in a case in which the rotation axis direction is parallel to the top long axis direction. The top movement amount decision unit 151 decides the product of the reconstruction axis length and the cosine of the tilt angle as a top movement amount in a case in which the apparatus is to execute step and shoot scanning upon tilting the gantry 100. FIG. 9 is a view showing an example of representing a top movement about b by a reconstruction axis length a and a tilt angle θ in a case in which the apparatus executes step and shoot scanning upon tilting the gantry 100 through the tilt angle θ. As shown in FIG. 9, the top movement amount b is calculated by the product of the reconstruction axis length a and the cosine (cos θ) of the tilt angle θ. Note that if the reconstruction axis length differs for each shoot, the top movement amount decision unit 151 can decide a top movement amount corresponding to each of a plurality of steps for each shoot.

A top driving unit 153 drives the top 119 to move the top 119 in the long axis direction in accordance with the decided top movement amount in step and shoot scanning.

The reconstruction unit 131 reconstructs volume data corresponding to the reconstruction region for each shoot.

(Step and Shooting Scan Function)

The step and shooting scan function is a function of deciding a top movement amount along the top long axis direction based on a reconstruction axis length, executing step and shooting scanning, and reconstructing volume data associated with a reconstruction region for each shoot.

Processing (to be referred to as step and shooting scan processing hereinafter) based on the step and shooting scan function will be described below.

Figure 10:
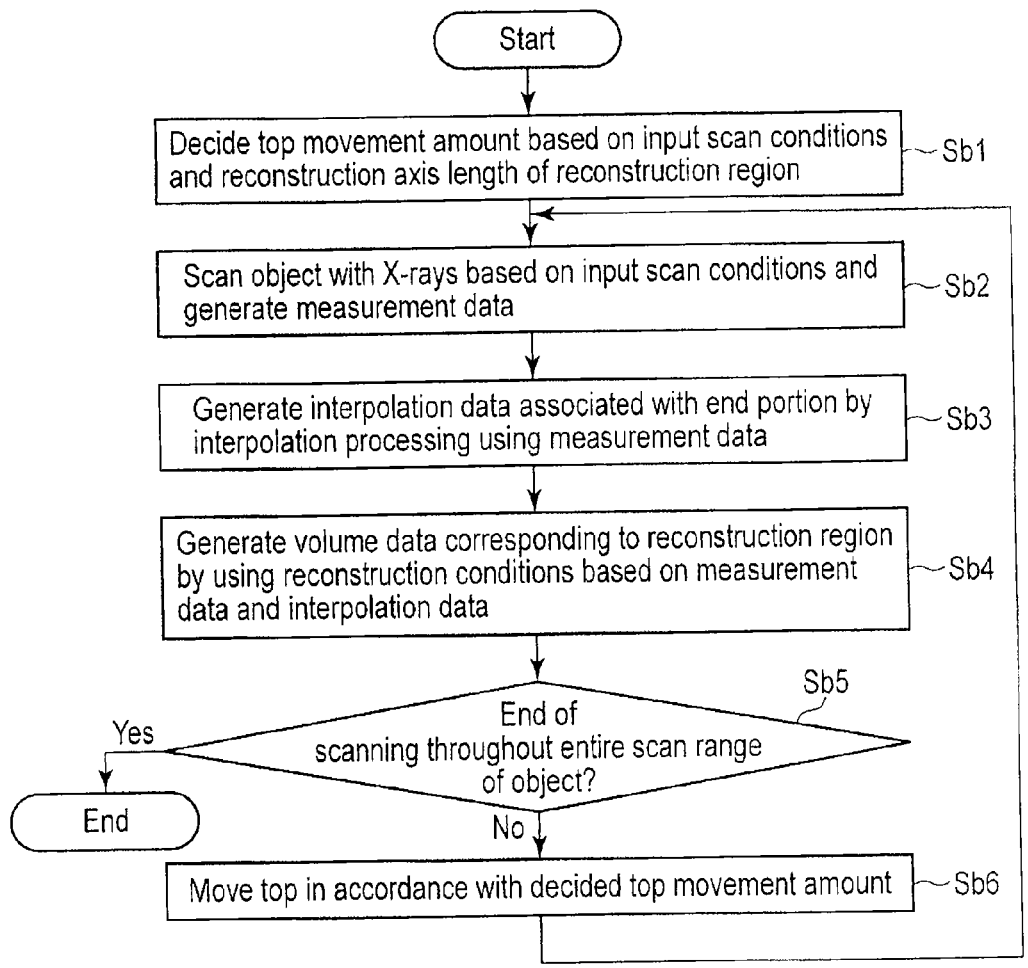
FIG. 10 is a flowchart showing an example of a scan procedure for step and shoot scanning according to a modification of the first embodiment.

FIG. 10 is a flowchart showing an example of a scan procedure in step and shooting scanning. After steps Sa1 to Sa3 in width decision reconstruction processing, the apparatus decides a top movement amount based on input scan conditions and reconstruction axis length (step Sb1). The apparatus scans an object with cone-beam X-rays in accordance with the input scan conditions to generate measurement data (step Sb2). The apparatus generates interpolation data associated with the measurement data unacquired region of an end portion by interpolation processing using the measurement data (step Sb3). The apparatus generates volume data associated with the reconstruction region by using the reconstruction conditions based on the measurement data and the interpolation data (step Sb4). If scanning throughout the entire scan range of the object under the scan conditions is not completed (step Sb5), the apparatus moves the top 119 in accordance with the decided top movement amount (step Sb6). The apparatus repeats steps Sb2 to Sb4. If scanning throughout the entire scan range of the object under the scan conditions is completed, the apparatus terminates step and shooting scanning.

The above arrangement can obtain the following effects.

The X-ray computed tomography apparatus 1 according to this embodiment can reconstruct volume data corresponding to a reconstruction region upon deciding the end portion width of the reconstruction region in accordance with a set radiation range (at least one of a cone angle, array count, and detector width), a diameter, the imaging target portion of an object, and the like. This makes it possible to reconstruct volume data approximated to a cylindrical shape as much as possible while maintaining the quality of a reconstructed image.

In addition, the X-ray computed tomography apparatus 1 according to this embodiment can decide a top movement amount based on a reconstruction axis length. In step and shooting scanning, the apparatus can minimize the overlap of volume data while increasing a step width. As described above, it is possible to reduce the radiation dose of an object while maintaining the quality of a reconstructed image.

Second Embodiment

The second embodiment differs from the first embodiment in that the apparatus decides the ratio of an end portion width (to be referred to as an end portion expansion ratio hereinafter) used for reconstruction to the maximum end portion width based on at least one of a diameter, set radiation range (at least one of a cone angle, array count, and detector width), and imaging target portion, and decides each end portion used for reconstruction based on the decided end portion expansion ratio.

FIG. 11 shows the arrangement of an X-ray computed tomography apparatus 1 according to the second embodiment. The X-ray computed tomography apparatus 1 according to the second embodiment includes a gantry 100, a high voltage generation unit 101, a preprocessing unit 125, an interpolation data generation unit 129, a reconstruction unit 131, a display unit 139, a control unit 143, an interface 133, an input unit 141, a ratio decision unit 155, and an end portion decision unit 157.

The ratio decision unit 155 decides an end portion expansion ratio based on the scan conditions and reconstruction condition used for reconstruction processing which are input via the input unit 141. More specifically, the ratio decision unit 155 includes a memory (not shown). The memory stores at least one of the first expansion ratio correspondence table between set radiation ranges (at least cone angles, array counts, or detector widths) and first end portion expansion ratios, the second expansion ratio correspondence table between diameters and second end portion expansion ratios, and the third expansion ratio correspondence table between imaging target portions and third end portion expansion ratios. The ratio decision unit 155 receives scan conditions and reconstruction conditions associated with the stored expansion ratio correspondence table and decides an end portion expansion ratio. For example, if the memory stores the first expansion ratio correspondence table, the ratio decision unit 155 decides an end portion expansion ratio based on the cone angle or the array count and the first expansion ratio correspondence table input via the input unit 141. The ratio decision unit 155 outputs the decided end portion expansion ratio to the end portion decision unit 157. Upon receiving, for example, an array count of 80 (or a detector width) corresponding to a cone angle of 4° via the input unit 141, the ratio decision unit 155 decides an end portion expansion ratio as 100%. In this case, the reconstruction region has a cylindrical shape.

Note that an end portion expansion ratio may be the ratio of the area of an end portion used for reconstruction to the maximum possible area of the end portion or the ratio of the length of the end portion used for reconstruction along the rotation axis direction to the length of the boundary line of the middle portion along the rotation axis direction.

The ratio decision unit 155 can also decide an imaging target portion in accordance with a synchronization target for a synchronous scan in a scan protocol and decide an end portion expansion ratio based on the decided imaging target portion. If, for example, a synchronous scan is an ECG scan, the ratio decision unit 155 decides a chest portion as an imaging target portion. In addition, if a synchronous scan is a respiratory gated scan, the ratio decision unit 155 decides an abdominal portion as an imaging target portion. The ratio decision unit 155 may also decide an imaging target portion in accordance with the reconstruction function setting. Note that the memory may store the fourth expansion ratio correspondence table between reconstruction functions and fourth end portion expansion ratios.

If the memory of the ratio decision unit 155 stores the first to fourth expansion ratio correspondence tables, the ratio decision unit 155 decides the first to fourth end portion expansion ratios respectively corresponding to the first to fourth expansion ratio correspondence tables based on the scan conditions and reconstruction conditions input via the input unit 141. More specifically, the ratio decision unit 155 reads out the first to fourth end portion expansion ratios respectively corresponding to the first to fourth expansion ratio correspondence tables based on the cone angle (array count or detector width), diameter, imaging target portion, and reconstruction function received from an RIS 135 and an HIS 137 via the input unit 141 or the interface 133. The ratio decision unit 155 decides, as an end portion expansion ratio associated with each end portion of the reconstruction region, the minimum one of the read first to fourth end portion expansion ratios.

Figure 12:
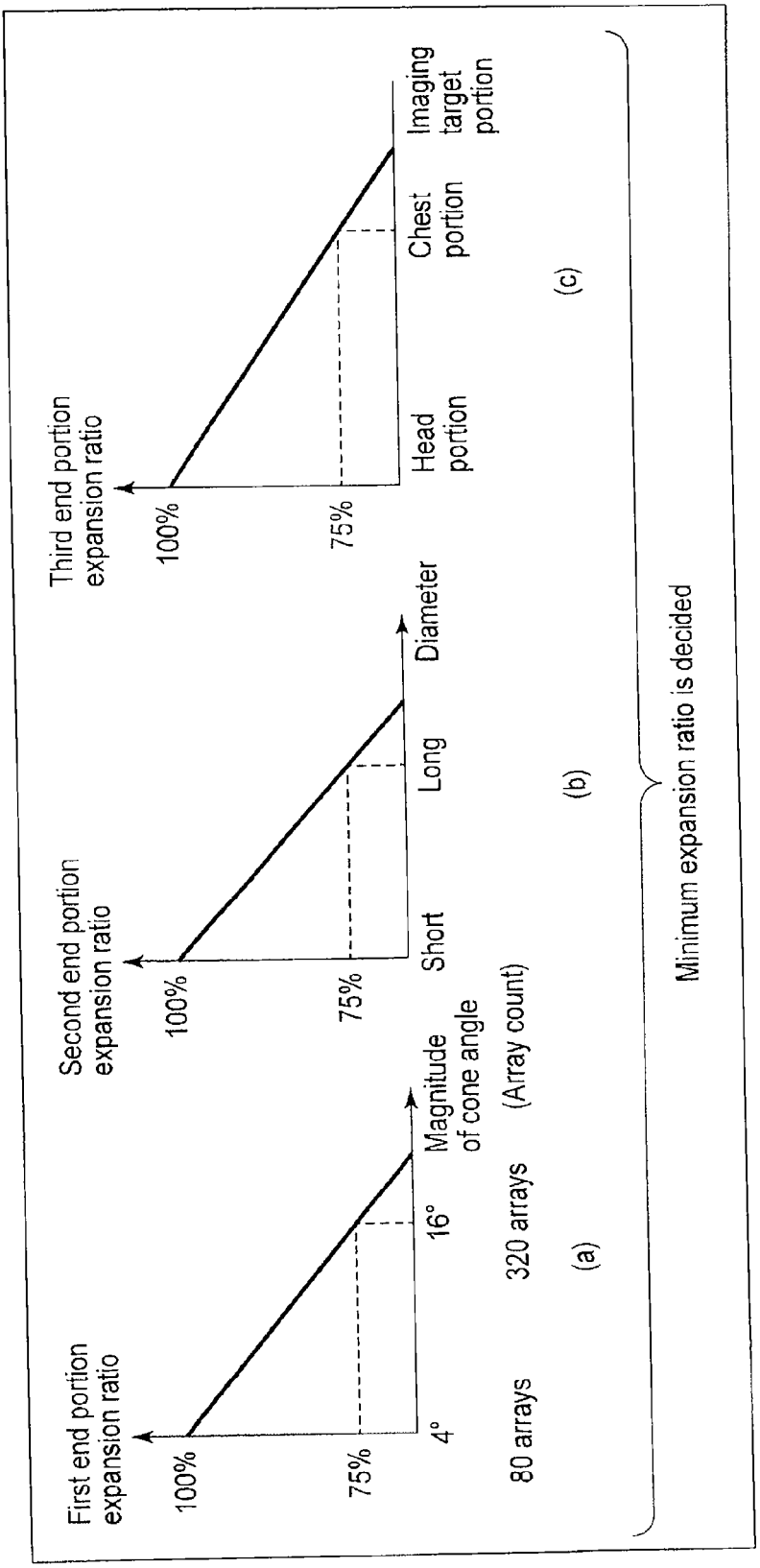
FIG. 12 is a view showing an example of the first to third expansion ratio correspondence tables according to the second embodiment.

FIG. 12 shows an example of a first expansion ratio correspondence table (a), a second expansion ratio correspondence table (b), and a third expansion ratio correspondence table (c). Note that the memory may store an end portion expansion ratio correspondence table (multivariable width correspondence table) corresponding to a plurality of types of conditions (a cone angle, array count, detector width, diameter, and imaging target portion) like those shown in FIG. 13 in place of the first to third expansion ratio correspondence tables.

The end portion decision unit 157 decides the region of each end portion used for reconstruction based on the end portion expansion ratio decided by the ratio decision unit 155. The end portion decision unit 157 outputs the decided region of the end portion to the interpolation data generation unit 129. The region of the end portion decided by the end portion decision unit 157 will be described with reference to FIGS. 14, 15, and 16 by exemplifying a case in which a middle portion on a slice including a rotation axis has a hexagonal sectional shape.

FIG. 14 is a view showing an example of a reconstruction region, mask regions, and a rotation axis when the expansion ratio is 0 or before an end portion expansion ratio is decided. In this case, the reconstruction region on the slice including the rotation axis is identical to a middle portion.

Figure 15:
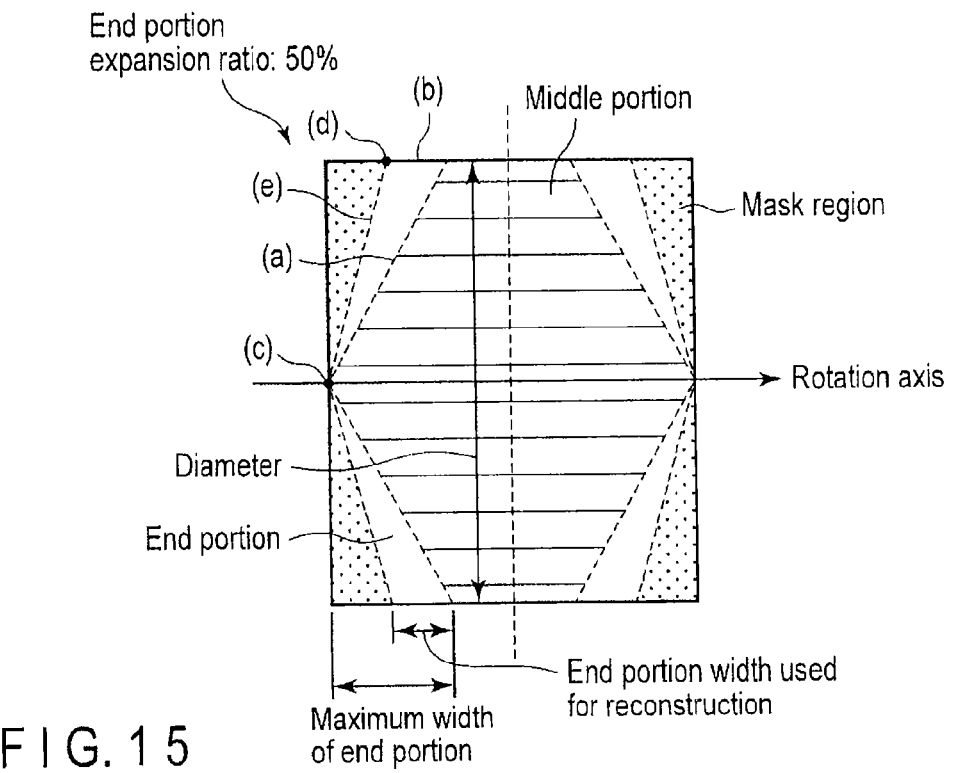
FIG. 15 is a view showing an example of a middle portion, end portions, mask regions, and a rotation axis when the expansion ratio is 50% according to the second embodiment.

FIG. 15 is a view showing an example of the end portion decided by the end portion decision unit 157, the middle portion, the mask regions, and the rotation axis when the end portion expansion ratio is 50% of the maximum width. The region of the end portion decided by the end portion decision unit 157 on a slice including a rotation axis is defined by sides (a), of the sides of a hexagon, which are not parallel to the rotation axis, sides (b) each of which has a length (end portion width) of 50% of the maximum width of the end portion and is parallel to the rotation axis, and sides (e) connecting vertices (c), of the vertices of the hexagon, which are located on the rotation axis to points (d) obtained by extending sides, of the six sides of the hexagon, which are parallel to the rotation axis throughout the end portion widths. The end portion expansion ratio decided by the ratio decision unit 155 is associated with the points (d) in FIG. 15.

Figure 16:
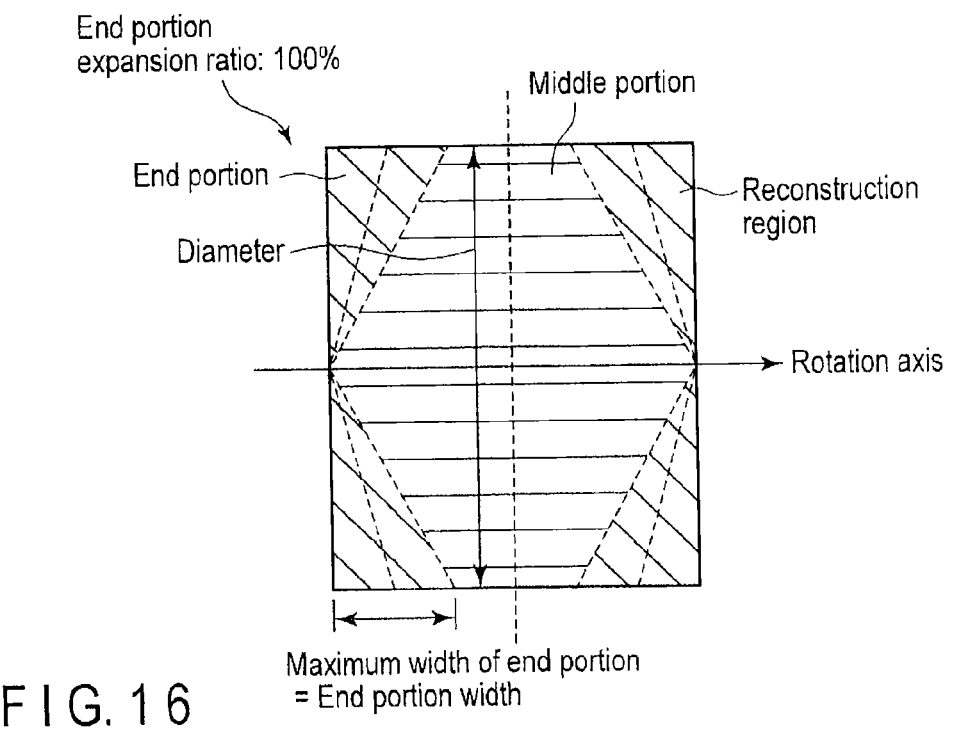
FIG. 16 is a view showing an example of a middle portion, end portions, and a rotation axis when the expansion ratio is 100% according to the second embodiment.

FIG. 16 is a view showing an example of end portions, a middle portion, and a rotation axis when the end portion expansion ratio is 100% (maximum width of end portion=end portion width). In this case, a reconstruction region on a slice including the rotation axis has a rectangular shape. The reconstruction region has a cylindrical shape in terms of three dimensions.

The interpolation data generation unit 129 interpolates the projection data associated with a measurement data unacquired region by using measurement data based on the region of each end portion output from the end portion decision unit 157.

(Expansion Ratio Decision Reconstruction Function)

The expansion ratio decision reconstruction function is a function of deciding an end portion expansion ratio based on at least scan conditions or reconstruction conditions and reconstructing the volume data associated with a reconstruction region. Processing based on the expansion ratio decision reconstruction function (to be referred to as expansion ratio decision reconstruction processing hereinafter) will be described below.

Figure 17:
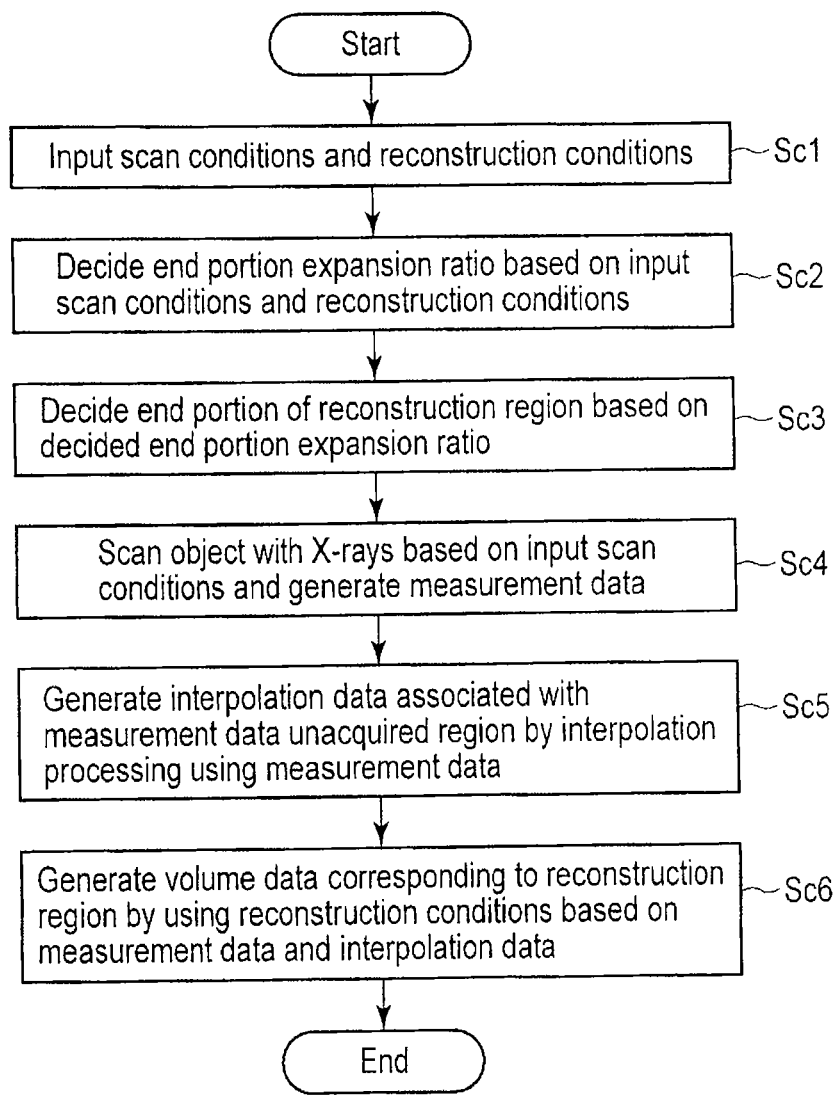
FIG. 17 is a flowchart showing an example of a procedure for expansion ratio decision reconstruction processing according to the second embodiment.
Figure 18:
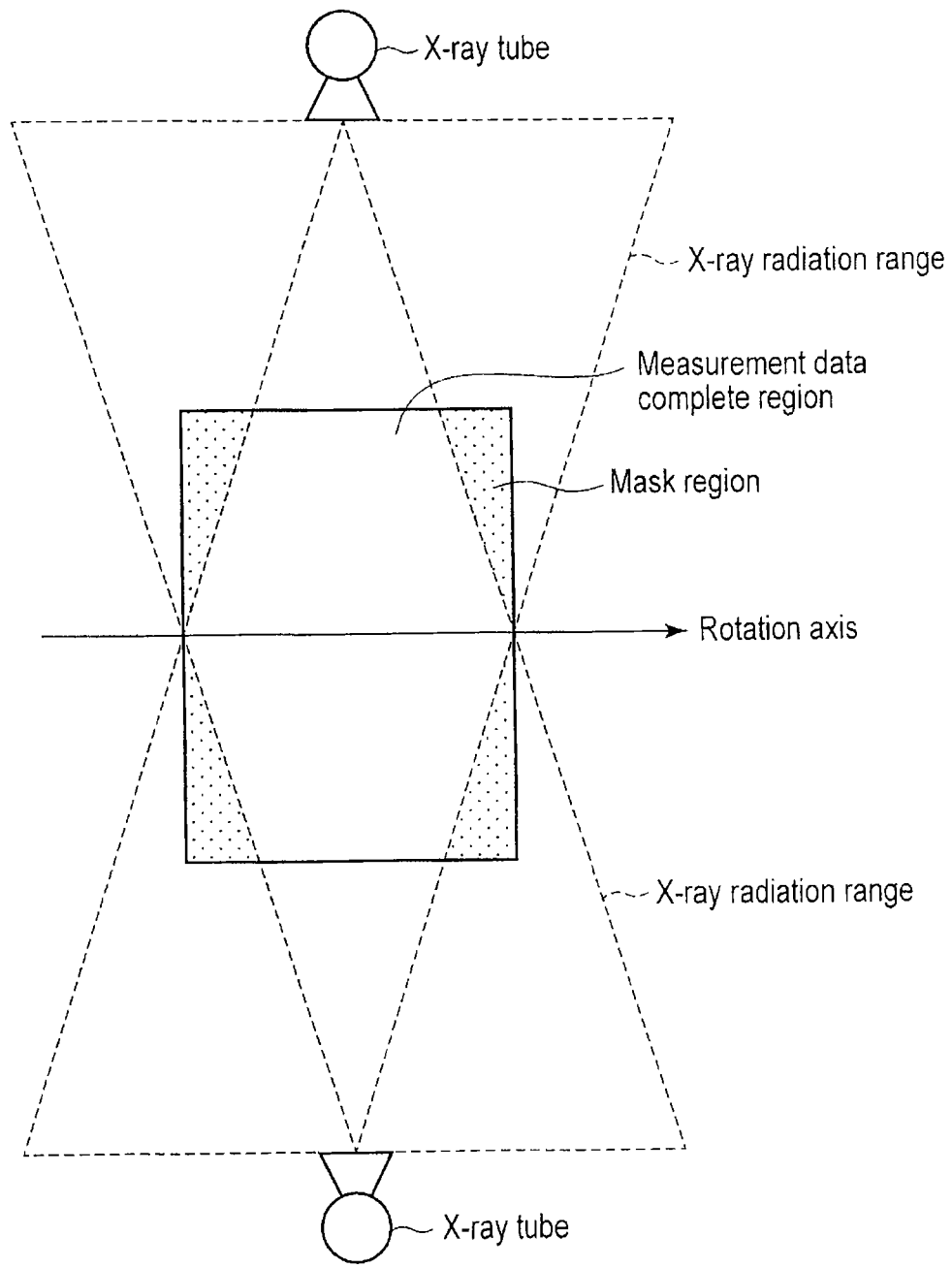
FIG. 18 is a view showing a measurement data complete region and mask regions together with an X-ray tube and an X-ray radiation range according to the prior art.

FIG. 17 is a flowchart showing an example of a procedure for expansion ratio decision reconstruction processing.

The apparatus executes scanography for an object. The operator inputs scan conditions, reconstruction conditions, and the like via the input unit 141 based on the image generated by scanography (step Sc1). The apparatus decides an end portion expansion ratio based on the input scan conditions and reconstruction conditions (step Sc2). The apparatus decides the region of each end portion used for reconstruction based on the decided end portion expansion ratio (step Sc3). The apparatus scans the object with cone-beam X-rays in accordance with the input scan conditions and generates measurement data (step Sc4). Interpolation processing using the measurement data generates interpolation data associated with the measurement data unacquired region of the end portion (step Sc5). The apparatus generates the volume data associated with the reconstruction region by using the reconstruction conditions based on the measurement data and the interpolation data (step Sc6).

The above arrangement can obtain the following effects.

The X-ray computed tomography apparatus 1 according to this embodiment can decide an end portion expansion ratio based on at least one of a cone angle (array count or detector width), diameter, and imaging target portion and decide the region of each end portion used for reconstruction based on the decided end portion expansion ratio. This makes it possible to reconstruct volume data approximated to a cylindrical shape as much as possible while maintaining the quality of a reconstructed image. As described above, it is possible to reduce the radiation dose of an object while maintaining the quality of a reconstructed image.

Note that each function according to each embodiment can be implemented by installing programs for executing the processing in a computer such as a workstation and expanding them in the memory. In this case, the programs which can cause the computer to execute the corresponding techniques can be distributed by being stored in storage media such as magnetic disks (Floppy® disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising:
   an X-ray generation unit configured to generate a cone-beam X-ray;
   a two-dimensional array type or multislice type X-ray detection unit configured to detect the X-ray from the X-ray generation unit through an object on a top;
   a reconstruction unit configured to reconstruct volume data for a reconstruction region, wherein the volume data is reconstructed based on projection data that corresponds to an output from the X-ray detection circuit, the reconstruction region having a diameter designated by an operator;

an interpolation data generation unit configured to generate interpolation data in order to interpolate the projection data of the reconstruction region; and a width decision unit configured to decide a width of end portions of an image, wherein the width of the end portions is decided based on: 1) the diameter of the reconstruction region, and at least one of 2) a set radiation range for radiation of the X-ray along a longitudinal direction of the top and 3) an imaging target portion of the object, the image is an image to be generated based on interpolation data and the projection data, and the end portions correspond to a region in which image quality of the image does not deteriorate.

2. The apparatus of claim 1, wherein the set radiation range corresponds to at least one of a cone angle, an array count of the X-ray detection unit, and a length of the X-ray detection unit along the longitudinal direction of the top.

3. The apparatus of claim 1, wherein the width decision unit is configured to decide, as the width of the end portions, a minimum width of a plurality of widths corresponding to the diameter of the reconstruction region, and at least one of the set radiation range, and the imaging target portion of the object, respectively.

4. The apparatus of claim 1, wherein the width decision unit is configured to decide the imaging target portion of the object based on at least one of a reconstruction function for reconstructing the volume data and the diameter of the reconstruction region, and wherein the width decision unit is configured to decide the width of the end portions based on the diameter, and at least one of the set radiation range and the decided imaging target portion.

5. The apparatus of claim 1, further comprising:

a top movement amount decision unit configured to decide a longitudinal movement amount of the top, wherein the longitudinal movement amount is decided based on a length of the reconstruction region in a rotation axis direction; and a top driving unit configured to drive the top to move in accordance with the decided movement amount.

6. An X-ray computed tomography apparatus comprising:

an X-ray generation unit configured to generate a cone-beam X-ray;

a two-dimensional array type or multislice type X-ray detection unit configured to detect the X-ray from the X-ray generation unit through an object on a top;

a reconstruction unit configured to reconstruct volume data for a reconstruction region, wherein the volume data is reconstructed based on projection data that corresponds to an output from the X-ray detection circuit, the reconstruction region having a diameter designated by an operator;

an interpolation data generation unit configured to generate interpolation data in order to interpolate the projection data of the reconstruction region;

a ratio decision unit configured to decide a width ratio, wherein the width ratio is decided based on the diameter of the reconstruction region, and at least one of a set radiation range for radiation of the X-ray along a longitudinal direction of the top and an imaging target portion of the object, wherein the width ratio is a ratio of a width of end portions of an image to a maximum width of the end portions determined based on the diameter of the reconstruction region and the set radiation range, the image is an image to be generated based on interpolation data and the projection data, and the end portions correspond to a region in which image quality of the image does not deteriorate; and an end portion decision unit configured to decide the end portions for reconstructing the volume data, based on the decided width ratio.

7. A reconstruction processing method comprising: reconstructing volume data for a reconstruction region, wherein the volume data is reconstructed based on projection data for an object on a top, the reconstruction region having a diameter designated by an operator; generating interpolation data in order to interpolate the projection data of the reconstruction region; and deciding a width of the end portions, wherein the width of end portions on an image is decided based on: 1) the diameter of the reconstruction region, an at least one of 2) a set radiation range for radiation of an X-ray along a longitudinal direction of the top and 3) an imaging target portion of the object, the image is an image to be generated based on interpolation data and the projection data, and the end portions correspond to a region in which image quality of the image does not deteriorate.

* * * * *